United States Patent
Ohi (10) Patent No.: US 9,348,033 B2
(45) Date of Patent: May 24, 2016

(54) POSITRON CT APPARATUS

(75) Inventor: Junichi Ohi, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 2034 days.

(21) Appl. No.: 12/519,152

(22) PCT Filed: Dec. 15, 2006

(86) PCT No.: PCT/JP2006/325064
§ 371 (c)(1),
(2), (4) Date: Jun. 12, 2009

(87) PCT Pub. No.: WO2008/072343
PCT Pub. Date: Jun. 19, 2008

(65) Prior Publication Data
US 2010/0027866 A1    Feb. 4, 2010

(51) Int. Cl.
*G06K 9/00* (2006.01)
*G01T 1/164* (2006.01)
*A61B 6/03* (2006.01)
*A61B 6/00* (2006.01)

(52) U.S. Cl.
CPC ............... *G01T 1/1644* (2013.01); *A61B 6/037* (2013.01); *G01T 1/1647* (2013.01); *A61B 6/03* (2013.01); *A61B 6/502* (2013.01)

(58) Field of Classification Search
USPC .................................. 382/128, 130–132, 154
See application file for complete search history.

(56) References Cited

U.S. PATENT DOCUMENTS

| | | | |
|---|---|---|---|
| 5,252,830 | A | 10/1993 | Weinberg |
| 5,451,789 | A | 9/1995 | Wong et al. |
| 6,144,759 | A | 11/2000 | Weese et al. |
| 6,545,280 | B2 * | 4/2003 | Weinberg ................ 250/363.02 |
| 6,915,004 | B2 * | 7/2005 | Newport et al. ............... 382/131 |
| 2003/0004413 | A1 * | 1/2003 | Inoue et al. .................... 600/436 |
| 2004/0183022 | A1 | 9/2004 | Weinberg |
| 2006/0108509 | A1 * | 5/2006 | Frangioni et al. .......... 250/208.1 |

FOREIGN PATENT DOCUMENTS

| | | |
|---|---|---|
| JP | 10-502169 A | 2/1998 |
| JP | 10-323347 A | 12/1998 |
| JP | 2000-75035 A | 3/2000 |

OTHER PUBLICATIONS

International Search Report for the Application No. PCT/JP2006/325064 mailed Mar. 20, 2007.

* cited by examiner

*Primary Examiner* — Weiwen Yang
(74) *Attorney, Agent, or Firm* — Cheng Law Group, PLLC (57) ABSTRACT

A positron CT apparatus of this invention includes a first detecting device and a first image processing device for acquiring a 3D image of a first site of interest. Further, a second detecting device and a second image processing device are provided for acquiring a real planar image of the first site of interest and a second site of interest. A calculated planar image calculating device calculates, based on the 3D image, data corresponding only to the first site of interest projected to the real planar image. A correcting device provides a corrected planar image corresponding only to the second site of interest by subtracting the calculated planar image from the real planar image. Thus, the 3D image corresponding to the first site of interest and the corrected planar image with a projection of the second site of interest can be acquired at the same time through one diagnosis.

8 Claims, 10 Drawing Sheets

POSITRON CT APPARATUS

CROSS-REFERENCE TO RELATED APPLICATIONS

The present application is a 371 of PCT International Application PCT/JP2006/325064, filed Dec. 15, 2006, the entire contents of which are hereby incorporated into this application by reference.

TECHNICAL FIELD

This invention relates to a positron CT apparatus which detects gamma rays emitted from a positron-emitting radioisotope (RI: Radio Isotope) distributed in the body of a patient, and more particularly to a technique for diagnosing two sites of interest at the same time.

BACKGROUND ART

A conventional positron CT apparatus (hereinafter called simply PET (Positron Emission Tomography) apparatus) will be described by way of example. The PET apparatus includes a detecting device having gamma-ray detectors arranged in a ring form for detecting gamma rays, and an image processor for producing an RI distribution image such as a sectional image or 3D image based on coincidence data obtained from results of detection by the detecting device. Each gamma-ray detector includes a scintillator having a two-dimensional arrangement of scintillator chips which emit light upon incidence of gamma rays, and a photomultiplier tube for converting the light emitted by the scintillator into electric signals. And a patient placed in the hollow of the detecting device is administered with a radioactive agent labeled with a positron-emitting radioisotope (RI: Radio Isotope). The positron-emitting radioisotope distributed in the body emits two gamma rays in 180-degree opposite directions. Each gamma-ray detector detects a gamma ray emitted out of the patient, and outputs an electric signal. The image processor produces an RI distribution image of the patient from data (hereinafter called coincidence data as appropriate) created when the electric signals are detected simultaneously (coincidence) in different positions (scintillator chips).

RI distribution images obtained from a whole-body PET apparatus having the above construction are useful for diagnosing mainly presence or absence, position, malignancy and so on of a tumor. However, since the hollow of the detecting device is about 65 cm to 90 cm in diameter, the RI distribution images have low resolution. Thus, it is usually difficult to determine tumors of 10 mm and less.

Figure 11:
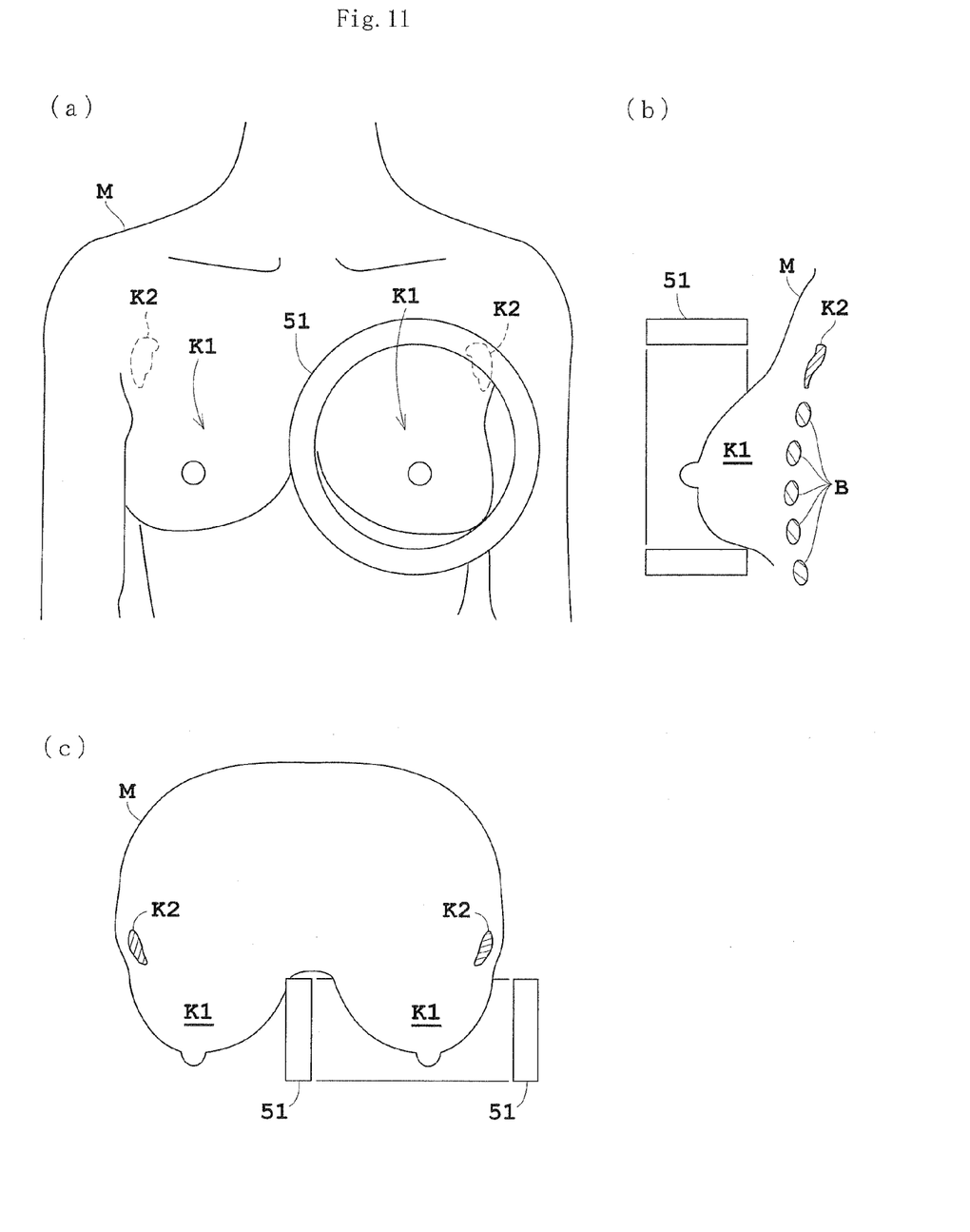

On the other hand, there are PET apparatus intended for diagnosis of only specific sites of interest of a patient, such as mammo-PET apparatus used exclusively for diagnosis of the breasts, for example. FIG. 11 (a) is a front view of a detecting device of a mammo-PET apparatus according to the prior art. FIG. 11 (b) is a view in vertical section thereof. FIG. 11 (c) is a view in horizontal section thereof. As shown, the detecting device 51 in a ring form has a reduced inside diameter (e.g. 18 cm), and gamma-ray detectors (not shown) arranged in the detecting device 51 are placed close to a breast (hereinafter referred to as "breast K1" as appropriate) which is a site of interest K1. Compared with the whole-body PET, this construction can discover and identify even a smaller tumor (see Patent Documents 1 and 2, for example).

[Patent Document 1]
Specification of U.S. Pat. No. 5,451,789
[Patent Document 2]
Specification of United States Patent Application Publication No. 2004/0183022

DISCLOSURE OF THE INVENTION

Problem to be Solved by the Invention

However, the conventional example with such construction has the following drawback.

Cancer which is a malignant tumor often metastasizes to lymph nodes, and therefore it is necessary to diagnose presence or absence of the tumor also in the nearby lymph node simultaneously with presence or absence of the tumor in the breast K1. The lymph node is a site of interest as is the breast K1. Particularly, a sentinel lymph node to which a lymph node metastasis of cancer takes place first often becomes a second site of interest K2 at the time of diagnosis of the breast K1. In the case of breast cancer, the axillary (armpit) lymph node (hereinafter referred to as "axillary lymph node K2" as appropriate) usually is the sentinel lymph node. However, as shown in FIG. 11, the axillary lymph node K2 is located adjacent the armpit at a short distance from the breast K1. With the detecting device 51 as shown in FIG. 11, therefore, the detection of gamma rays is obstructed by the nearby arm and ribs B (see FIG. 11 (b)), and the axillary lymph node cannot be diagnosed well.

It is therefore necessary to diagnose the axillary lymph node with a gamma camera for exclusive use in detecting single photons, separately from a diagnosis with the mammo-PET apparatus, or to carry out a biopsy of the sentinel lymph node K2 separately. Thus, even with the conventional mammo-PET apparatus, there is an inconvenience that it cannot diagnose at the same time the two sites of interest, such as the breast K1 and the sentinel lymph node K2 thereof. As a result, there is an inconvenience that the patient M is subject to a large burden.

Further, in the case of the breasts, it is necessary to diagnose separately the right and left breasts K1, respectively. This worsens each of the above inconveniences.

This invention has been made having regard to the state of the art noted above, and its object is to provide a positron CT apparatus which can diagnose two different sites of interest at the same time.

Means for Solving the Problem

To fulfill the above object, this invention provides the following construction.

A positron CT apparatus according to this invention is a positron CT apparatus for detecting gamma rays released from a patient, comprising a first detecting device for detecting gamma rays around a first site of interest of the patient; a second detecting device for detecting gamma rays, which is disposed separately across part of the first site of interest and a second site of interest spaced from an imaging area of the first detecting device; a first image processing device for producing an RI distribution image from coincidence data obtained from the first detecting device; a second image processing device for producing a real planar image corresponding to gamma rays released in a predetermined projecting direction, based on coincidence data obtained from the second detecting device; a calculated planar image calculating device for calculating, based on the RI distribution image produced, a calculated planar image of a time when the imaging area of the first detecting device is projected in the same direction as the projecting direction; and a correcting device for subtracting the calculated planar image from the real planar image.

According to the positron CT apparatus of this invention, with the first detecting device and second detecting device provided, the first site of interest can be set to a position in the imaging area of the first detecting device, and the second site of interest to a position in the imaging area of the second detecting device and spaced from the imaging area of the first detecting device. The first and second detecting devices arranged in this way detect gamma rays at the same time. With the first image processing device, an RI distribution image corresponding to the imaging area of the first detecting device can be produced. This RI distribution image allows the first site of interest to be diagnosed effectively.

With the second image processing device, calculated planar image calculating device and correction device, a real planar image corresponding to the imaging area of the second detecting device is produced, a calculated planar image with a projection of only the imaging area of the first detecting device is calculated, and the calculated planar image is subtracted from the real planar image, thereby obtaining a planar image corresponding to the imaging area of the second detecting device and the area spaced from the imaging area of the first detecting device. This corrected planar image allows the second site of interest also to be diagnosed. Thus, since the RI distribution image and corrected planar image can be acquired through one diagnosis about the two different, first and second sites of interest, the burden of the patient can also be reduced.

In the positron CT apparatus of this invention, it is preferred that the first site of interest is a breast, and the second site of interest is a sentinel lymph node of the breast. It is then possible to diagnose, for example, presence or absence of a tumor in positions of the breast and sentinel lymph node.

In the positron CT apparatus of this invention, it is preferred that the second detecting device has an imaging area thereof obliquely crossing the imaging area of the first detecting device. In a positional relationship such as of the breast and sentinel lymph node, whichever site of interest can be approached.

In the positron CT apparatus of this invention, it is preferred that the second detecting device is in an opposed arrangement. The real planar image can be produced for the entire imaging area of the second detecting device.

In the positron CT apparatus of this invention, it is preferred that the first detecting device acts also as one part of the second detecting device arranged separately, and the second image processing device produces the real planar image based on coincidence data obtained from the second detecting device and the first detecting device. The imaging area of the second detecting device can be enlarged efficiently.

In the positron CT apparatus of this invention, it is preferred that the second detecting device is arranged at opposite sides of the first detecting device. The imaging area of the second detecting device can be formed effectively.

In the positron CT apparatus of this invention, it is preferred that the first detecting device is arranged in a ring form or polygonally. Gamma rays released from around the first site of interest can be detected effectively.

In the positron CT apparatus of this invention, it is preferred that the RI distribution image is a 3D image. The first site of interest can be diagnosed effectively.

A positron CT apparatus according to this invention is a positron CT apparatus for detecting gamma rays released from a patient, comprising a combined connecting detecting device having two ring detecting devices ring-shaped and connected at an angle to each other for detecting gamma rays; and an image processing device for producing an RI distribution image for each of the ring detecting devices based on coincidence data obtained from the combined detecting device.

According to the positron CT apparatus of this invention, a diagnosis relating to presence or absence of a tumor, for example, can be carried out at the same time for a pair of sites of interest such as the breasts and sites of interest different from them.

In the positron CT apparatus of this invention, it is preferred that the combined detecting device surrounds a pair of right and left breasts and sentinel lymph nodes of the respective breasts simultaneously. It is then possible to diagnose, for example, presence or absence of a tumor in positions of the breasts and sentinel lymph nodes.

In the positron CT apparatus of this invention, it is preferred that the two ring detecting devices cross each other without obstructing imaging areas of the ring detecting devices. An RI distribution image for each of the ring detecting devices can be obtained conveniently.

This specification discloses an invention relating to the following positron CT apparatus also:

(1) The positron CT apparatus according to any one of claims 1 to 6, wherein the first detecting device is arranged separately across the first site of interest, the apparatus further comprising a drive mechanism for moving the first detecting device around the first site of interest.

According to the invention set out in (1) above, with the first detecting device being moved by the drive mechanism, the first detecting device can detect gamma rays around the first site of interest.

Effects of the Invention

According to the positron CT apparatus of this invention, with the first detecting device and second detecting device provided, the first site of interest can be set to a position in the imaging area of the first detecting device, and the second site of interest to a position in the imaging area of the second detecting device and spaced from the imaging area of the first detecting device. The first and second detecting devices arranged in this way detect gamma rays at the same time. With the first image processing device, a 3D image corresponding to the imaging area of the first detecting device can be produced. This 3D image allows the first site of interest to be diagnosed effectively.

BRIEF DESCRIPTION OF THE DRAWINGS

FIG. 2 (a) is a plan view of a first and a second detecting devices;

FIG. 2 (b) is a view in vertical section taken on line A-A of FIG. 2 (a);

FIG. 6 (a) is a plan view of a first and a second detecting devices;

FIG. 6 (b) is a view in vertical section taken on line A-A of FIG. 6 (a);

FIG. 10 (*a*) is a plan view of a first and a second detecting devices according to a modified embodiment;

FIG. 10 (*b*) is a view in vertical section taken on line A-A of FIG. 10 (*a*);

FIG. 11 (*a*) is a front view of a detecting device of a mammo-PET apparatus according to the prior art;

FIG. 11 (*b*) is a view in vertical section thereof; and

FIG. 11 (*c*) is a view in horizontal section thereof.

DESCRIPTION OF REFERENCES 1, 2 . . . first detecting device
3 . . . second detecting device
5 . . . combined detecting device
6, 7 . . . ring detecting units
16 . . . image processor
21 . . . first image processing unit
23 . . . second image processing unit
25 . . . calculated planar image calculating unit
27 . . . correcting unit
M . . . patient
K1 . . . first site of interest
K2 . . . second site of interest
A1 . . . first imaging area
A2 . . . second imaging area

BEST MODE FOR CARRYING OUT THE INVENTION

The object of diagnosing two different sites of interest at the same time has been fulfilled by a positron CT apparatus for detecting gamma rays released from a patient, comprising a first detecting device for detecting gamma rays around a first site of interest of the patient; a second detecting device for detecting gamma rays, which is disposed separately across part of the first site of interest and a second site of interest spaced from an imaging area of the first detecting device; a first image processing device for producing an RI distribution image from coincidence data obtained from the first detecting device; a second image processing device for producing a real planar image corresponding to gamma rays released in a predetermined projecting direction, based on coincidence data obtained from the second detecting device; a calculated planar image calculating device for calculating, based on the RI distribution image produced, a calculated planar image of a time when the imaging area of the first detecting device is projected in the same direction as the projecting direction; and a correcting device for subtracting the calculated planar image from the real planar image.

Embodiment 1

Embodiment 1 of this invention will be described hereinafter with reference to the drawings.

Figure 1:
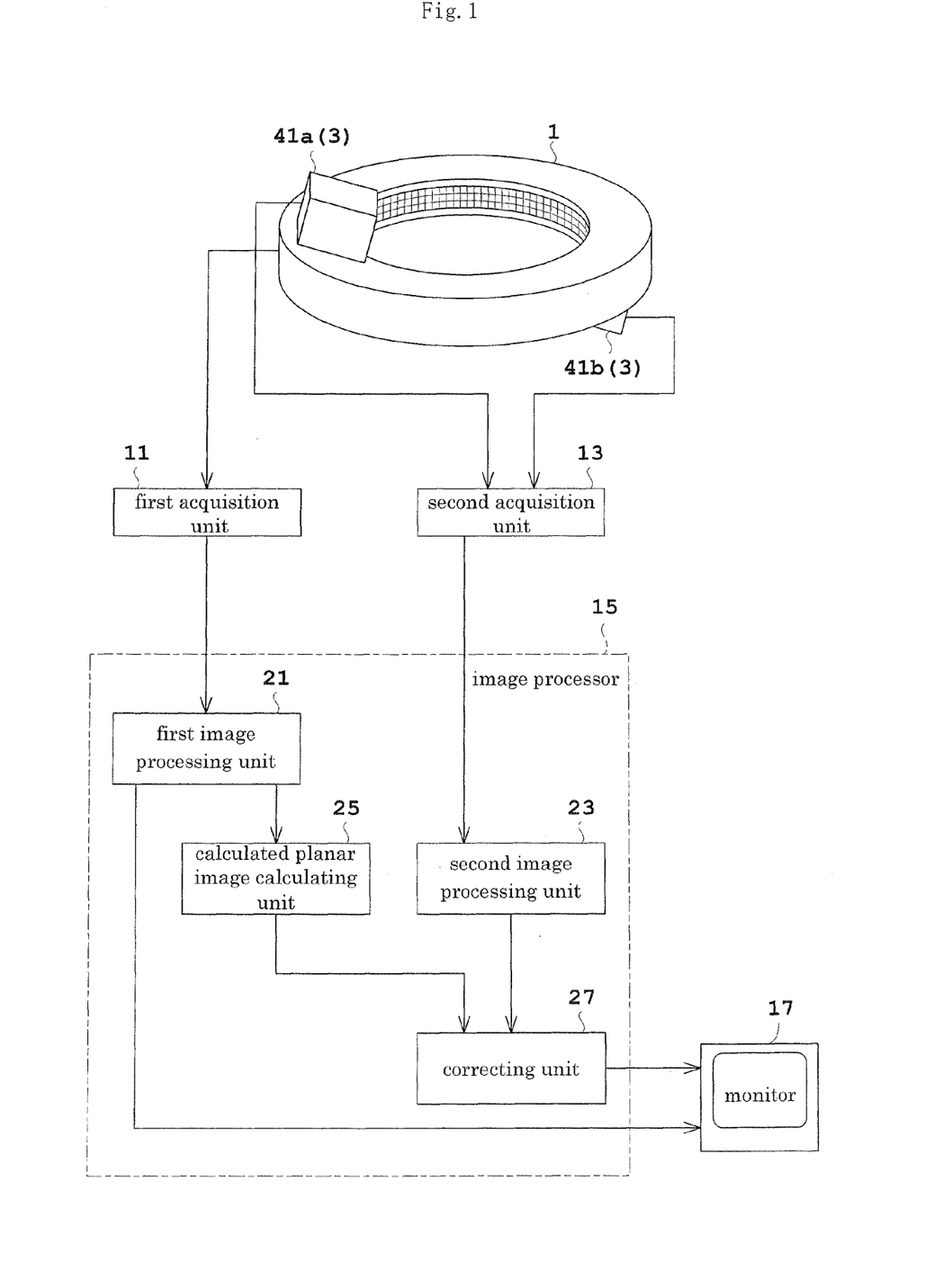
FIG. 1 is a block diagram showing an outline of a PET apparatus according to Embodiment 1.
Figure 2:
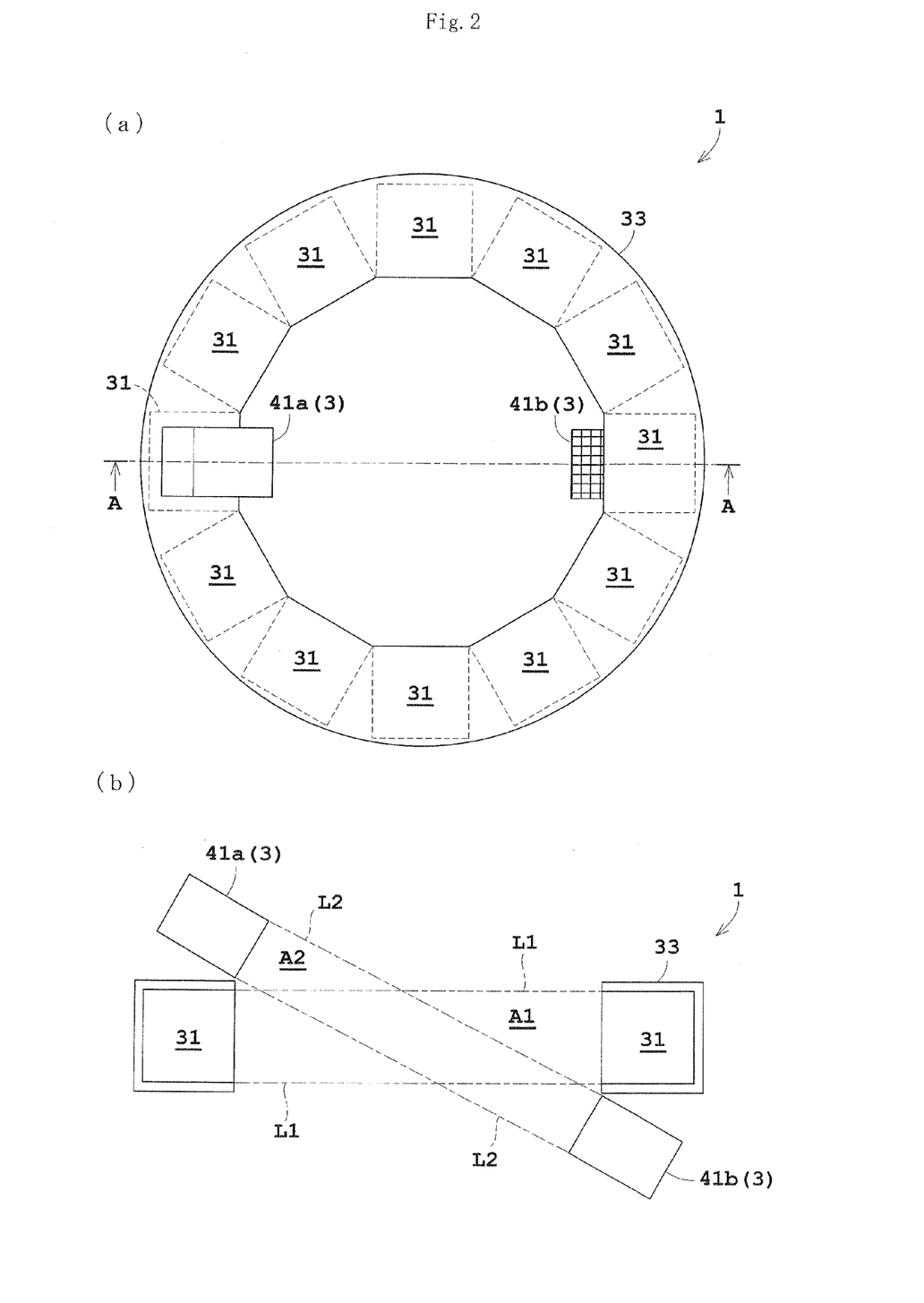
Figure 3:
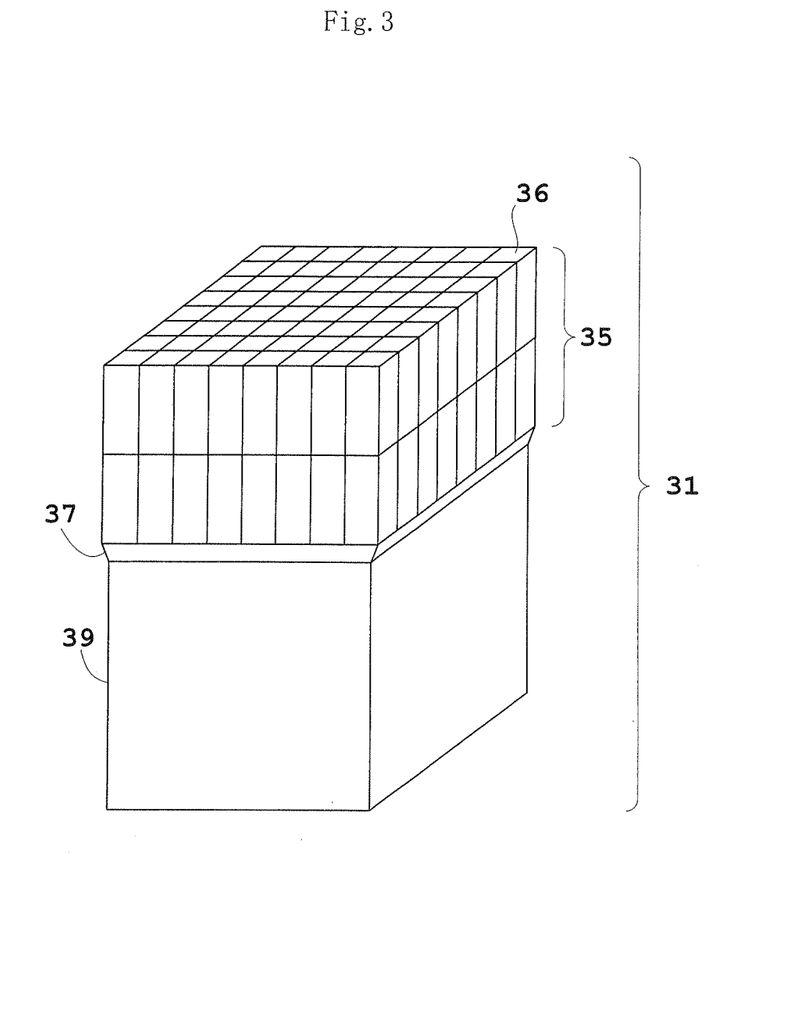
FIG. 3 is a perspective view of a gamma-ray detector.

FIG. 1 is a block diagram showing an outline of a PET (Positron Emission Tomography) apparatus according to Embodiment 1. FIG. 2 (*a*) is a plan view of a first and a second detecting devices. FIG. 2 (*b*) is a view in vertical section taken on line A-A of FIG. 2 (*a*). FIG. 3 is a perspective view of a gamma-ray detector. This embodiment will be described, taking as an example of PET apparatus a positron CT apparatus which diagnoses a breast of a patient (human body) M as a first site of interest K1, and an axillary lymph node which is the sentinel lymph node of the breast as a second site of interest K2.

The PET apparatus according to this embodiment includes a first detecting device 1, a second detecting device 3, a first acquisition unit 11, a second acquisition unit 13, an image processor 15 and a monitor 17. The image processor 15 has a first and a second image processing units 21 and 23, a calculated planar image calculating unit 25 and a correcting unit 27.

The first detecting device 1 is ring-shaped, and detects gamma rays around the first site of interest K1. The first detecting device 1 has a hollow portion whose inside diameter is about 180 mm, for example. As shown in FIG. 2, the first detecting device 1 has a plurality of gamma-ray detectors 31 arranged in a circle (in the form of a ring), and a housing 33 for accommodating and holding the gamma-ray detectors 31. In this specification, an imaging area of the first detecting device 1 surrounded by the detecting planes of the gamma-ray detectors 31 is called the first imaging area A1. The first imaging area A1 is a range bounded by two chain lines L1 in FIG. 2 (*b*), and corresponds to the hollow portion of the first detecting device 1.

As shown in FIG. 3, each gamma-ray detector 31 is constructed of a scintillator 35 for converting gamma rays into light, a light guide 37 for leading the light to a photomultiplier 39, and the photomultiplier 39 which converts the light into electric signals. The scintillator 35 is an aggregate of scintillator chips 36 and, as shown, is in the form of an array having a matrix arrangement (e.g. eight rows×eight columns) stacked in a plurality of stages (e.g. two stages). In the case of illustrated scintillator 35, the first detecting device 1 becomes a multilayer ring with eight layers of scintillator chips 36 arranged in the ring form.

The second detecting device 3 has detector blocks 41*a* and 41*b* arranged separately at opposite sides of the first detecting device 1 for detecting gamma rays. The detector blocks 41*a* and 41*b* are positioned such that an imaging area A2 of the second detecting device 3 bounded by the detecting planes thereof (hereinafter called simply the second imaging area, which corresponds to the range bounded by two chain lines L2 in FIG. 2) crosses part of the first imaging area A1 noted above, and includes also areas outside the first imaging area A1. In this embodiment, the detector blocks 41*a* and 41*b* are arranged in positions symmetrical about a point adjacent the center of the hollow portion of the first detecting device 1. The second imaging area A2 is formed to cross the first imaging area A1 obliquely. Further, in this embodiment, the detecting planes of the detector blocks 41*a* and 41 are arranged parallel and opposed to each other. These detector blocks 41*a* and 41*b* also are constructed of the gamma-ray detectors 31 described above.

The first and second acquisition units 11 and 13 acquire coincidence data from the electric signals outputted from the first and second detecting devices 1 and 3, respectively.

Next, each processing unit of the image processor 15 will be described. The first image processing unit 21 carries out a reconstruction process based on the coincidence data acquired by the first acquisition unit 11, to produce a 3D image.

The second image processing unit 23 produces a planar image based on the coincidence data acquired by the second acquisition unit 13. Here, the planar image is a two-dimensional image produced based only on the coincidence data corresponding to gamma rays released parallel to a predetermined projecting direction, among coincidence data acquired by detecting gamma rays released in arbitrary directions. In other words, it is a two-dimensional image obtained by projecting a positron-emitting radioisotope in a predetermined projecting direction. Here, the projecting direction may be set, selected or varied as appropriate. In this embodiment, the projecting direction is set to a direction perpendicular to the detecting planes of the detector blocks 41*a* and 41*b*. In this case, the projecting direction is the same direction as the chain lines L2 shown in FIG. 2 (*b*), and a planar image can be produced for the whole of the second imaging area A2. In other words, the whole of the second imaging area A2 serves as an effective imaging area. In the following description, the planar image produced by the second image processing unit 23 will be called the real planar image for distinguishment from a calculated planar image described hereinafter.

The calculated planar image calculating unit 25 calculates a calculated planar image occurring when only the first imaging area A1 is projected in the same direction as the projecting direction, based on the 3D image produced by the first image processing unit 21. More particularly, it presumes, by calculation, a calculated planar image which could be obtained if the second image processing unit 23 produced a planar image based only on the positron-emitting radioisotope distributed over the first imaging area A1.

Here, the 3D image is based on results of detection by the first detecting device 1, and the real planar image to be presumed is based on results of detection by the second detecting device 3. Therefore, when calculating the calculated planar image based on the 3D image, a sensitivity ratio of the first and second detecting devices 1 and 3 is taken into consideration. This sensitivity ratio has a value set beforehand based on actual measurement results. Specifically, a radiation source of gamma rays whose strength is known is placed in a position where the first and second imaging areas A1 and A2 overlap, an actual measurement is carried out with the first and second detecting devices 1 and 3, and a ratio of coincidence data (collection counts) corresponding to the first and second detecting devices 1 and 3 is set as the sensitivity ratio.

The correcting unit 27 carries out a process of acquiring a corrected planar image by subtracting the calculated planar image calculated by the calculated planar image calculating unit 25 from the real planar image produced by the second image processing unit 23.

The 3D image and corrected planar image produced are outputted to the monitor 17 as appropriate.

The above first and second acquisition units 11 and 13 and image processor 15 are realized by a central processing unit (CPU) for reading and executing a predetermined program, and storage media such as a RAM (Random-Access Memory) and a fixed disk for storing a variety of information.

Figure 4:
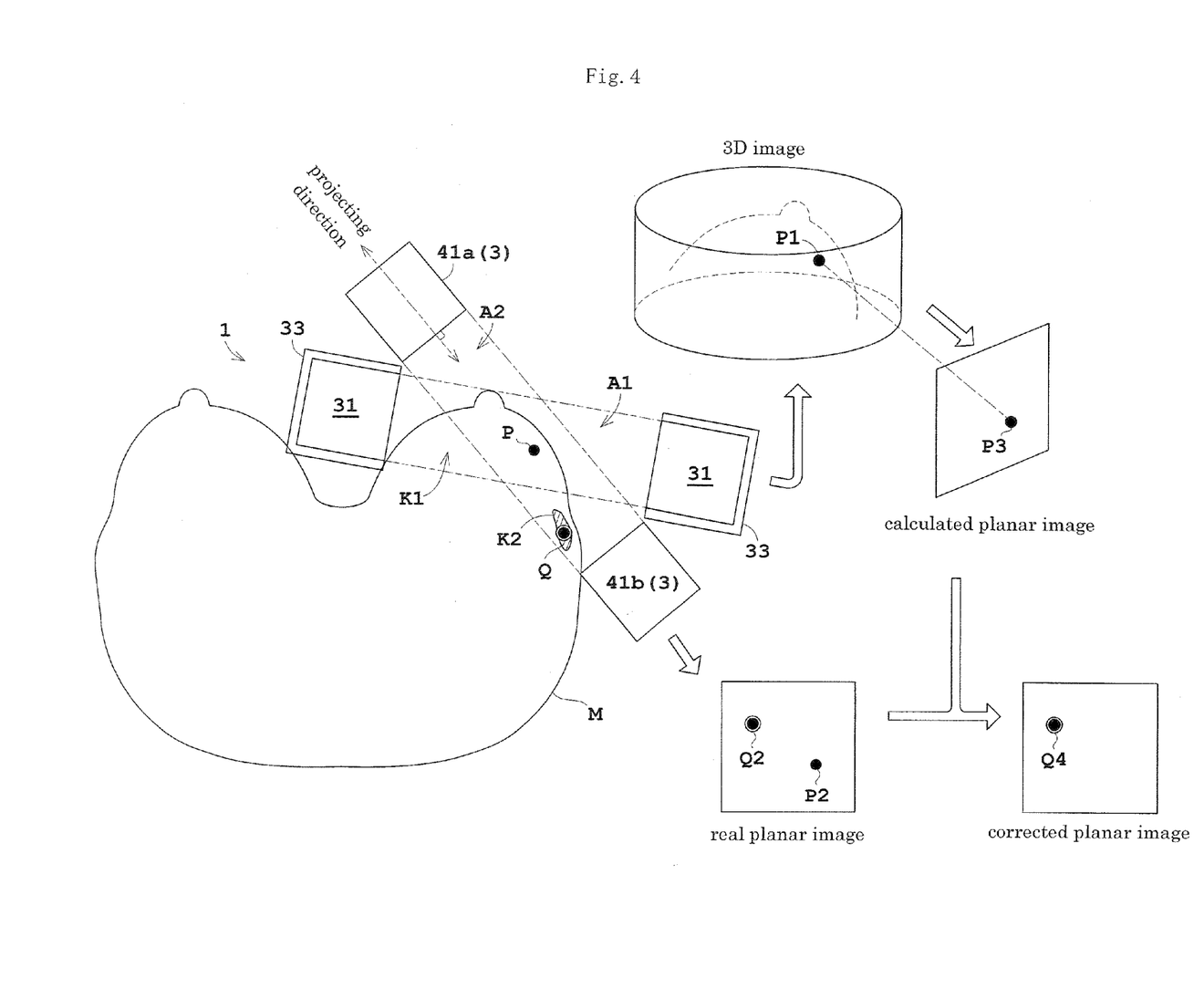
FIG. 4 is a view schematically showing a flow of producing a 3D image of a first site of interest and a corrected planar image of a second site of interest.

Next, operation of the PET apparatus according to Embodiment 1 will be described referring to FIG. 4. FIG. 4 is a view schematically showing a flow of producing the 3D image of the first site of interest and the corrected planar image of the second site of interest.

As shown in FIG. 4, the first site of interest (breast) K1 is placed in the first imaging area A1, and the first and second detecting devices 1 and 3 are positioned so that the second site of interest (axillary lymph node) K2 may be inserted in the second imaging area A2 and in an area spaced from the first imaging area A1.

Next, the patient M is injected with a radioactive substance labeled with a positron-emitting radioisotope. The positron-emitting radioisotope releases two gamma rays in the patient M in 180-degrees opposite directions. The first and second detecting devices 1 and 3 detect the gamma rays released out of the patient M and having reached the detecting planes, and output electric signals, respectively.

FIG. 4 illustrates positions of accumulation of positron-emitting radioisotope P and Q. The positron-emitting radioisotope P has accumulated in the first site of interest K1, and its position is in an area where the first and second imaging areas A1 and A2 overlap. The positron-emitting radioisotope Q has accumulated in the second site of interest K2, and its position is in the second imaging area A2 and in an area spaced from the first imaging area A1. In this case, the gamma rays released from the positron-emitting radioisotope P can be detected by the first and second detecting devices 1 and 3. The gamma rays released from the positron-emitting radioisotope Q can be detected only by the second detecting device 3.

The first and second acquisition units 11 and 13 obtain coincidence data from results of detection by the first and second detecting devices 1 and 3, respectively. Specifically, electric signals outputted from the first and second detecting devices 1 and 3 are once successively recorded in memory along with position information and time information. The data is read from the memory with fixed timing to determine coincidence events, and the events are counted to obtain coincidence data.

The first image processing unit 21 carries out a reconstruction process based on the coincidence data corresponding to the first detecting device 1, to produce the 3D image. As the reconstruction process, an existing technique is employed as appropriate such as filtered back projection, iterative approximation method, 3D Fourier transform, 3D-FBP, rebinning, 3D reprojection or FORE (Fourier rebinning).

FIG. 4 shows a schematic view of the 3D image produced by the first image processing unit 21. The 3D image has data corresponding to the first imaging area A1, and includes coincidence data (collection count) corresponding to the positron-emitting radioisotope P and its three-dimensional position information. The 3D image shown in FIG. 4 includes a position corresponding to the positron-emitting radioisotope P, which is schematically shown with sign "P1" affixed thereto.

The second image processing unit 23 selects, as effective data, only the coincidence data corresponding to the gamma rays released in the predetermined projecting direction among the coincidence data acquired from the results of detection by the second detecting device 3. And based on the selected coincidence data, it produces the real planar image corresponding to the projecting direction.

FIG. 4 shows a schematic view of the real planar image produced by the second image processing unit 23. The real planar image has data corresponding to the second imaging area A2, and includes coincidence data (collection count) corresponding to positron-emitting radioisotope P and Q and its two-dimensional position information. The real planar image shown in FIG. 4 includes positions corresponding to positron-emitting radioisotope P and Q, which are schematically shown with signs "P2" and "Q2" affixed thereto.

The calculated planar image calculating unit 25 calculates the calculated planar image as follows. First, considering the relative positional relationship of the first and second detecting devices 1 and 3, a data range corresponding to an area where the first and second imaging areas A1 and A2 overlap in the 3D image is determined. Next, the 3D image corresponding to the determined data range is compressed in the same direction as the projecting direction of the real planar image, to convert it into a two-dimensional image. Further, considering the sensitivity ratio of the first and second detecting devices 1 and 3, the coincidence data (collection count) of the radioisotope distributed on the two-dimensional image is corrected to obtain the calculated planar image.

FIG. 4 shows a schematic view of the calculated planar image calculated by the calculated planar image calculating unit 25. The calculated planar image has data corresponding to the area where the first and second imaging areas A1 and A2 overlap, and includes the coincidence data (collection count) corresponding to the positron-emitting radioisotope P and its two-dimensional position information. As noted above, the coincidence data is what the sensitivity ratio of the first and second detecting devices 1 and 3 is taken into consideration with respect to the results of detection by the first detecting device 1. The calculated planar image shown in FIG. 4 includes a position corresponding to point P1, which is schematically shown with sign "P3" affixed thereto.

The correcting unit 27 subtracts the calculated planar image from the real planar image, to cancel the coincidence data corresponding to the positron-emitting radioisotope distributed over the first imaging area A1. As a result, the corrected planar image has a projection of only the positron-emitting radioisotope distributed over an area excluding the first imaging area A1 from the second imaging area A2.

FIG. 4 shows a schematic view of the corrected planar image obtained from the correcting unit 27. The corrected planar image has data corresponding to the area excluding the first imaging area A1 from the second imaging area A2, and includes coincidence data (collection count) corresponding to the positron-emitting radioisotope Q and its two-dimensional position information. A position corresponding to the positron-emitting radioisotope Q is schematically shown with sign "Q4" affixed thereto.

The 3D image and corrected planar image produced are outputted to the monitor 17 as appropriate.

Thus, the PET apparatus according to Embodiment 1 includes the first detecting device 1 having the first imaging area A1, and the second detecting device 3 having the second imaging area A2 crossing part of the first imaging area A1 and including also areas spaced from the first imaging area A1. Consequently, the first and second detecting devices 1 and 3 can be installed to place the first site of interest (breast) K1 in the first imaging area A1, and the second site of interest (axillary lymph node) K2 in the second imaging area A2 and in a position spaced from the first imaging area A1. Therefore, the first and second detecting devices 1 and 3 can detect gamma rays at the same time. And with the first image processing unit 21 provided for producing a 3D image corresponding to the first detecting device 1, presence or absence, and position (three-dimensional position), of the positron-emitting radioisotope in the first imaging area A1, a grade of malignancy and so on can be diagnosed properly. With the second image processing unit 23 for producing a real planar image corresponding to the second detecting device 3, the calculated planar image calculating unit 25 for calculating a calculated planar image from the 3D image corresponding to the first detecting device 1, and the correcting unit 27 for subtracting the above calculated planar image from the real planar image corresponding to the second detecting device 3, presence or absence, and position (two-dimensional position), of the positron-emitting radioisotope in the second imaging area A2, a grade of malignancy and so on can also be diagnosed properly. Thus, the PET apparatus according to this embodiment having each component can diagnose the two different, first site of interest (breast) K1 and second site of interest (axillary lymph node) K2 at the same time. As a result, the burden of the patient M can also be reduced.

Since the second imaging area A2 is formed to cross the first imaging area A1 obliquely, the first and second detecting devices 1 and 3 can be arranged conveniently so that the axillary lymph node which is the second site of interest K2 may be located in the second imaging areas A2 and in a position spaced from the first imaging area A1.

Since the second detecting device 3 is opposed, that is, the detector blocks 41a and 41b are arranged to have the detecting planes parallel and opposed to each other, the whole of the second imaging area A2 can serve as an effective imaging area.

Embodiment 2

Next, Embodiment 2 of this invention will be described with reference to the drawings.

Figure 5:
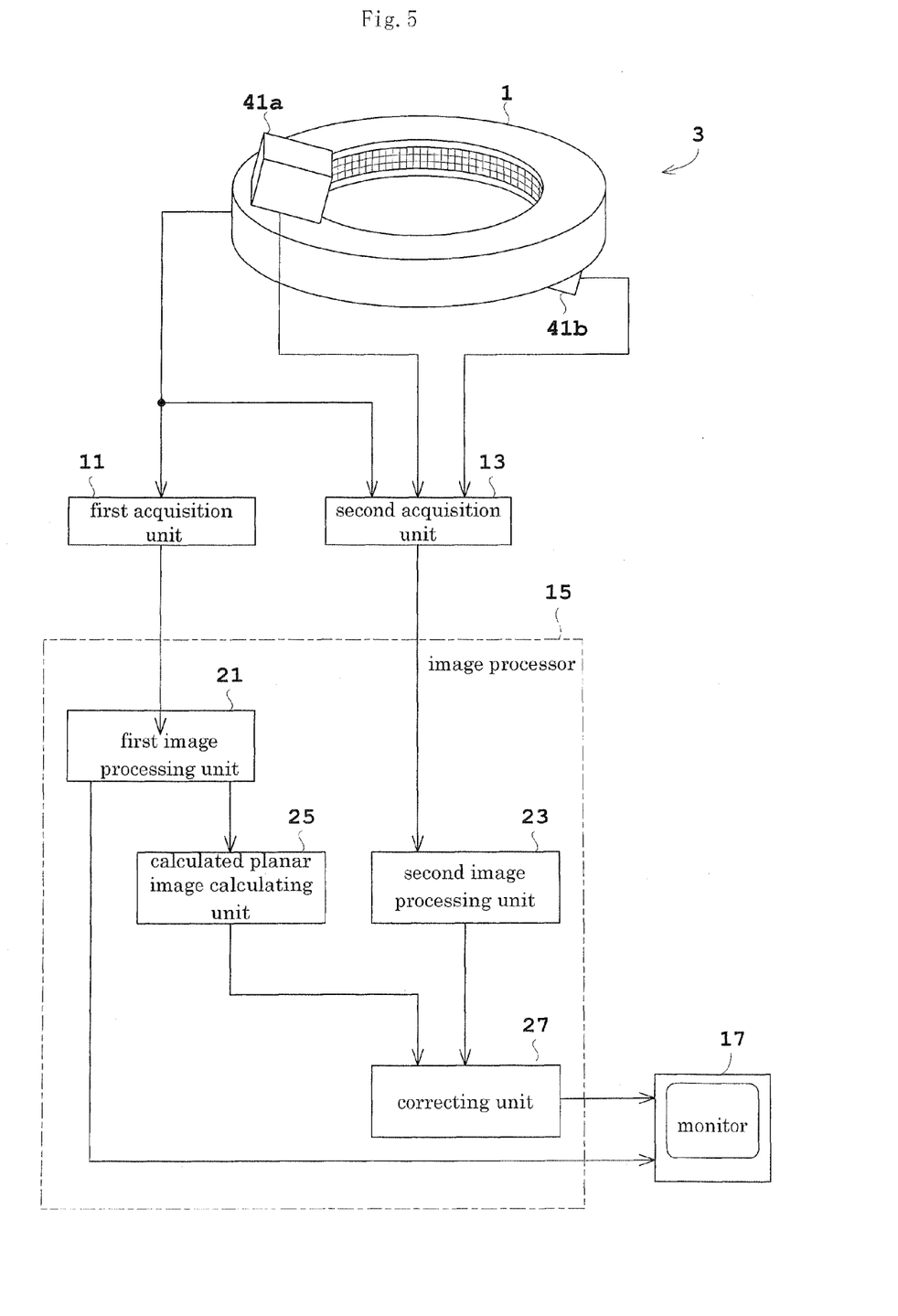
FIG. 5 is a block diagram showing an outline of a PET apparatus according to Embodiment 2.
Figure 6:
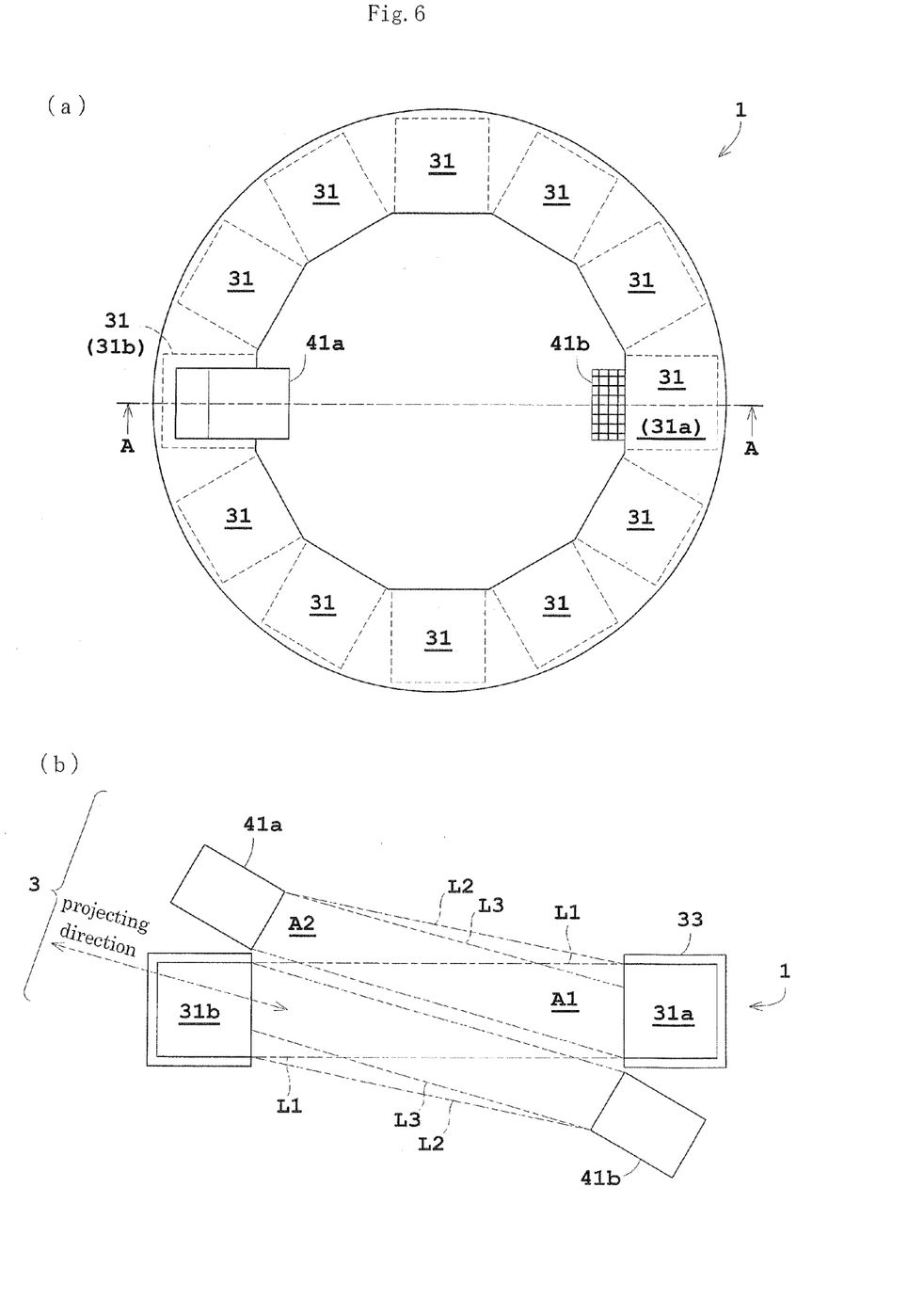

FIG. 5 is a block diagram showing an outline of a PET (Positron Emission Tomography) apparatus according to Embodiment 2. FIG. 6 (a) is a plan view of a first and a second detecting devices. FIG. 6 (b) is a view in vertical section taken on line A-A of FIG. 6 (a). Embodiment 2 also will be described, taking as an example of PET apparatus a positron CT apparatus which diagnoses a breast of a patient (human body) M as a first site of interest K1, and an axillary lymph node which is the sentinel lymph node of the breast as a second site of interest K2. Components identical to those of Embodiment 1 are shown with the same signs, and will not particularly be described.

Reference is made to FIG. 6. The second detecting device 3 according to Embodiment 2 includes detector blocks 41a and 41b arranged separately at opposite sides of the first detecting device 1, and the first detecting device 1 opposed to the respective detector blocks 41a and 42b. The relationship between the detector blocks 41a and 42b and the first detecting device 1 opposed thereto is sufficient if coincidence data can be acquired through coincidence counting of gamma rays released in substantially 180-degrees opposite directions. Their detecting planes may be parallel or may not be parallel. FIG. 6 (b) shows a case of not being parallel. And in the arrangement shown in FIG. 6, the whole of the first detecting device 1, i.e. all the gamma-ray detectors 31 arranged in the ring form, are in an opposed relationship to the detector blocks 41a and 41b, and can carry out coincidence counting of gamma rays in combination with the detector blocks 41a and 41b. Thus, in Embodiment 2, the first detecting device 1 serves as part of the second detecting device 3 to function also as one side of the second detecting device 3 arranged separately.

For expediency of description, the second detecting device 3 will be described hereinafter as being constructed of pairs of gamma-ray detector 31a and detector block 41a, and gamma-ray detector 31b and detector block 41b. In this case, the second imaging area A2 of the second detecting device 3 is an area bounded by the detecting planes of the detector blocks 41a and 41b and gamma-ray detectors 31a and 31b, and corresponds to the range bounded by two chain lines L2 shown in FIG. 6 (b). Here, the projecting direction set by the second image processing unit 23 is not parallel to the chain lines L2, as shown in FIG. 6 (b), the effective imaging area of the second detecting device 3 is a range enabling acquisition of coincidence data, which is defined by the second imaging area A2 and the projecting direction, i.e. the range bounded by two chain lines L3.

Reference is made to FIG. 5. The first acquisition unit 11 acquires coincidence data from the electric signals outputted from the first detecting device 1. The second acquisition unit 13 acquires coincidence data from the electric signals outputted from part of the first detecting device 1 (gamma-ray detectors 31a and 31b) acting also as the second detecting device 3, and from the detector blocks 41a and 41b, respectively.

The second image processing unit 23 produces a real planar image based on the coincidence data acquired by the second collection unit 13. Here, the real planar image is produced by projecting the coincidence data corresponding to the gamma rays released parallel to a predetermined projecting direction, on a plane selected and set as appropriate. The plane selected and set as appropriate is, for example, a plane perpendicular to the projecting direction, or a plane parallel to the detecting planes of the detector blocks 41a and 41b or gamma-ray detectors 31a and 31b. However, the plane of projection is not limited to this.

Figure 7:
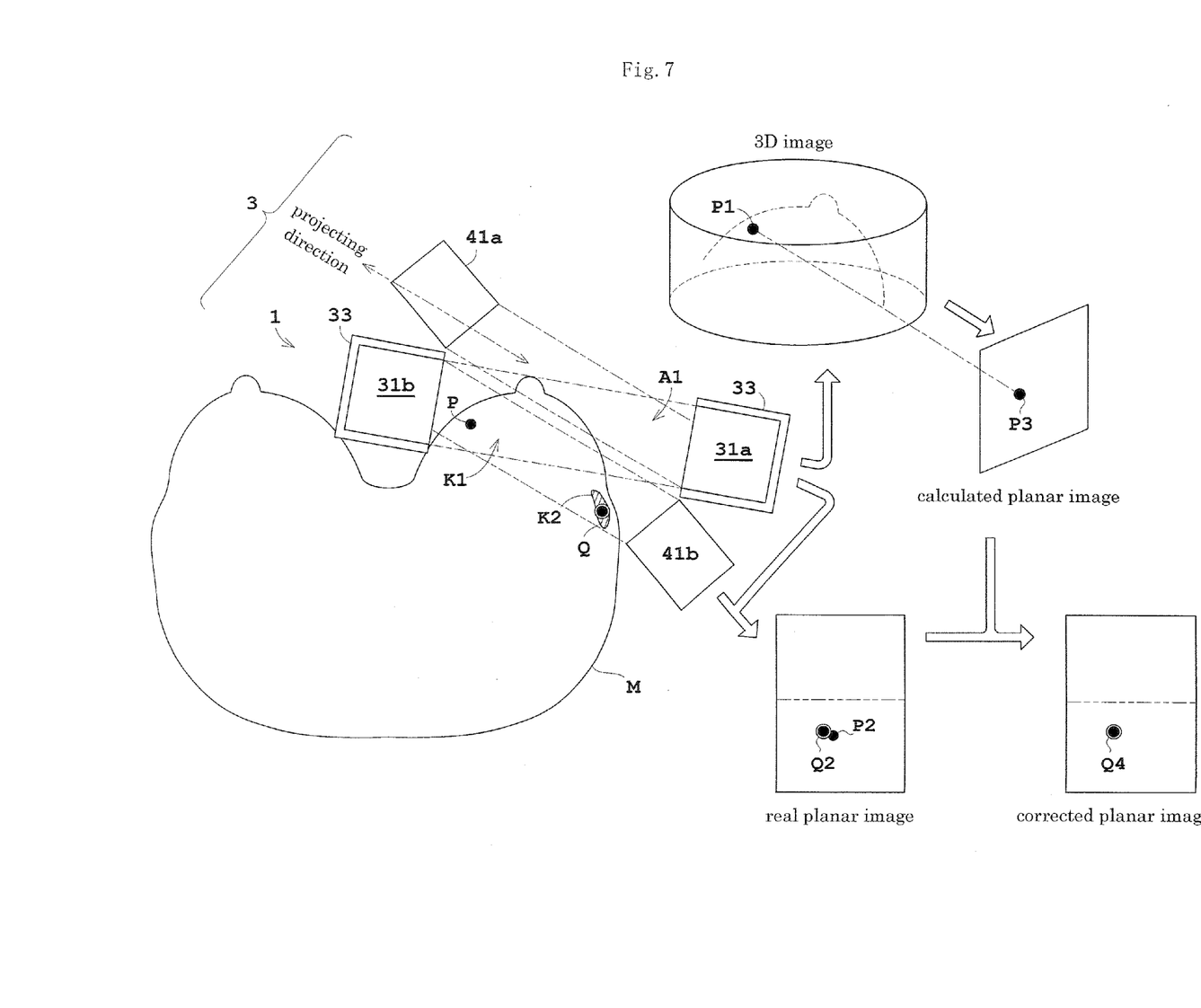
FIG. 7 is a view schematically showing a flow of producing a 3D image of a first site of interest and a corrected planar image of a second site of interest.

Next, operation of the PET apparatus according to Embodiment 2 will be described referring to FIG. 7. FIG. 7 is a view schematically showing a flow of producing a 3D image of the first site of interest and a corrected planar image of the second site of interest.

As shown in FIG. 7, the first site of interest (breast) K1 is placed in the first imaging area A1, and the first detecting device 1 and detector blocks 41a and 41b are positioned so that the second site of interest (axillary lymph node) K2 may be inserted in the effective imaging area of the second detecting device 3 and in an area spaced from the first imaging area A1.

Next, the patient M is injected with a radioactive substance. The first and second detecting devices 1 and 3 detect gamma rays, and output electric signals, respectively.

FIG. 7 illustrates positions of accumulation of positron-emitting radioisotope P and Q. The positron-emitting radioisotope P has accumulated in the first site of interest K1, and its position is in an area where the first imaging area A1 and the effective imaging area of the second detecting device 3 overlap. The positron-emitting radioisotope Q has accumulated in the second site of interest K2, and its position is in the effective imaging area of the second detecting device 3 and in an area spaced from the first imaging area A1. In this case, the gamma rays released from the positron-emitting radioisotope P can be detected by the first detecting device 1 and detector blocks 41a and 41b. The gamma rays released from the positron-emitting radioisotope Q can be detected only by the second detecting device 3 (gamma-ray detectors 31a and 31b and detector blocks 41a and 41b).

The first acquisition unit 11 obtains coincidence data from results of detection by the first detecting device 1. The second acquisition unit 13 obtains coincidence data from results of detection by the second detecting device 3.

The first image processing unit 21 carries out a reconstruction process based on the coincidence data corresponding to the first detecting device 1, to produce the 3D image. FIG. 7 shows a schematic view of the 3D image produced by the first image processing unit 21.

The second image processing unit 23 produces the real planar image based on the coincidence data acquired from the results of detection by the second detecting device 3.

FIG. 7 shows a schematic view of the real planar image produced by the second image processing unit 23. The real planar image is a combination of planar images obtained from the pair of detector block 41a and gamma-ray detector 31a and the pair of detector block 41b and gamma-ray detector 31b. FIG. 7 schematically shows a connecting part in a two-dot chain line. FIG. 7 schematically shows also an overlap of positions P2 and Q2 corresponding to the positron-emitting radioisotope P and Q.

The calculated planar image calculating unit 25 calculates the calculated planar image as follows. First, the 3D image is compressed in the projecting direction to convert it into a two-dimensional image. Next, considering the sensitivity ratio of the first and second detecting devices 1 and 3, the coincidence data (collection count) of the radioisotope distributed on the planar image is corrected to obtain the calculated planar image. FIG. 7 schematically shows the calculated planar image calculated by the calculated planar image calculating unit 25.

The correcting unit 27 carries out an alignment of the real planar image and calculated planar image by taking into consideration the relative positional relationship between the first and second detecting devices 1 and 3. Then, the calculated planar image is subtracted from the real planar image, to cancel the coincidence data corresponding to the positron-emitting radioisotope distributed over the first imaging area A1. As a result, the corrected planar image has a projection of only the positron-emitting radioisotope distributed over an area excluding the first imaging area A1 from the effective imaging area of the second detecting device 3. Even if the real planar image has an overlap of the positron-emitting radioisotope distributed in the area spaced from the first imaging area A1 and in the first imaging area A1, the coincidence data corresponding to the positron-emitting radioisotope distributed in the first imaging area A1 can be canceled appropriately. FIG. 7 shows a schematic view of the corrected planar image obtained from the correcting unit 27.

Thus, the PET apparatus according to Embodiment 2 includes the first detecting device 1 having the first imaging area A1, and the second detecting device 3 having the effective imaging area crossing part of the first imaging area A1 and including also areas spaced from the first imaging area A1. Consequently, the two different, first and second sites of interest K1 and K2 can be diagnosed at the same time. That is, the first and second detecting devices 1 and 3 can be installed to place the first site of interest (breast) K1 in the first imaging area A1, and the second site of interest (axillary lymph node) K2 in the effective imaging area of the second detecting device 3 and in a position spaced from the first imaging area A1. Therefore, the first and second detecting devices 1 and 3 can detect gamma rays at the same time. And with the first image processing unit 21 provided for producing a 3D image corresponding to the first detecting device 1, presence or absence, and position (three-dimensional position), of the positron-emitting radioisotope in the first imaging area A1, a grade of malignancy and so on can be diagnosed properly. With the second image processing unit 23 for producing a real planar image corresponding to the second detecting device 3, the calculated planar image calculating unit 25 for calculating a calculated planar image from the 3D image corresponding to the first detecting device 1, and the correcting unit 27 for subtracting the above calculated planar image from the real planar image corresponding to the second detecting device 3, presence or absence, and position (two-dimensional position), of the positron-emitting radioisotope in the second imaging area A2, a grade of malignancy and so on can also be diagnosed properly. Thus, the PET apparatus according to this embodiment having each component can diagnose the two different, first site of interest (breast) K1 and second site of interest (axillary lymph node) K2 at the same time.

Since the first detecting device 1 acts also as part of the second detecting device 3, the second imaging area A2 of the second detecting device 3 can be enlarged efficiently.

Embodiment 3

Next, Embodiment 3 of this invention will be described with reference to the drawings.

Figure 8:
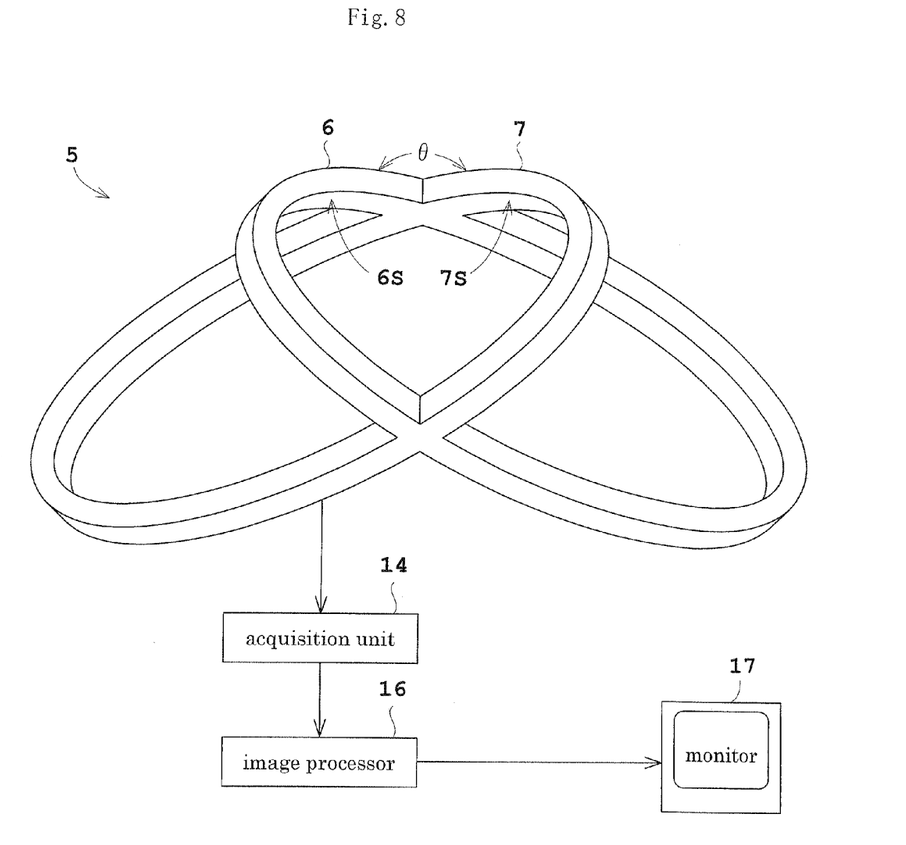
FIG. 8 is a block diagram showing an outline of a PET apparatus according to Embodiment 3.
Figure 9:
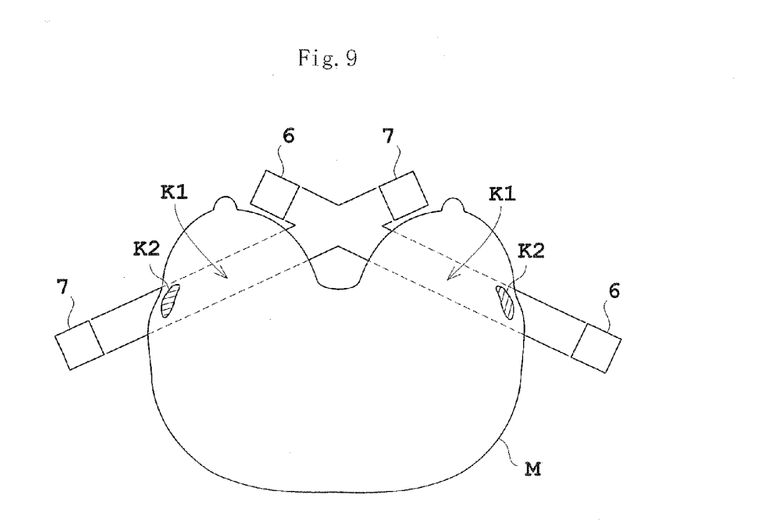
FIG. 9 is a sectional view of a detecting device of the PET apparatus according to Embodiment 3.

FIG. 8 is a block diagram showing an outline of a PET apparatus according to Embodiment 3. FIG. 9 is a sectional view of a detecting device according to Embodiment 3. Embodiment 3 will be described, taking as an example of PET apparatus a positron CT apparatus which diagnoses, all at the same time, the pair of right and left breasts of a patient (human body) M as a first site of interest K1, and the pair of right and left axillary lymph nodes as a second site of interest K2. Components identical to those of Embodiment 1 are shown with the same signs, and will not particularly be described.

The PET apparatus according to this embodiment includes a combined detecting device 5, a acquisition unit 14, an image processor 16 and a monitor 17.

The combined detecting device 5 according to Embodiment 3 has two ring detecting units 6 and 7 with the same ring shape for detecting gamma rays. The ring detecting units 6 and 7 are connected to have slice surfaces forming an angle θ, and cross each other at two locations not to obstruct imaging areas of the ring detecting units 6 and 7. Each of the ring detecting units 6 and 7 has a hollow portion whose inside diameter is about 180 mm, for example. Each of the ring detecting units 6 and 7 has an arrangement of gamma-ray detectors 31 (not shown in FIG. 8). Each of the inner peripheral surfaces 6S and 7S of the ring detecting units 6 and 7 defines detecting planes with scintillator chips 36 (not shown in FIG. 8) arranged in multiple layers. The gamma-ray detectors 31 arranged in positions where the ring detecting units 6 and 7 cross are shared by the ring detecting units 6 and 7. The ring detecting units 6 and 7 correspond to the ring detecting devices in this invention.

The acquisition unit 14 acquires coincidence data from electric signals outputted from the ring detecting units 6 and 7.

The image processor 16 carries out a reconstruction process based on the coincidence data acquired by the collector 14. Through this process a 3D image is produced for each of the ring detecting units 6 and 7.

The 3D images produced are outputted to the monitor 17 as appropriate.

The above acquisition unit 14 and image processor 16 are realized by a central processing unit (CPU) for reading and executing a predetermined program, and storage media such as a RAM (Random-Access Memory) and a fixed disk for storing a variety of information.

Next, operation of the PET apparatus according to Embodiment 3 will be described referring to FIG. 9.

As shown, the combined detecting device 5 is placed so that the respective ring detecting units 6 and 7 may cover, at the same time, the first site of interest (breast) K1 and second site of interest (axillary lymph node) K2 at one side, and the first site of interest (breast) K1 and second site of interest (axillary lymph node) K2 at the other side.

Next, the patient M is injected with a radioactive substance. The ring detecting units 6 and 7 detect gamma rays, and output electric signals, respectively.

The acquisition unit 14 acquires coincidence data from the results of detection by the ring detecting units 6 and 7.

The image processor 16 carries out a reconstruction process based on the coincidence data corresponding to the ring detecting units 6 and 7, to produce a 3D image for each of the ring detecting units 6 and 7. Each 3D image obtained has data corresponding to the area bounded by each of the inner peripheral surfaces of the ring detecting units 6 and 7, and includes coincidence data (collection count) corresponding to the positron-emitting radioisotope distributed in the first and second sites of interest K1 and K2 and its three-dimensional position information.

The two 3D images produced are outputted to the monitor 17 as appropriate.

Thus, with the PET apparatus according to Embodiment 3, the combined detecting device 5 having the two ring detecting units 6 and 7 connected at an angle to each other can cover all of the pair of right and left breasts and two axillary lymph nodes corresponding to the breasts. And the ring detecting units 6 and 7 can detect gamma rays at the same time, and the image processor 16 can produce two 3D images corresponding to the ring detecting units 6 and 7. It is therefore possible to diagnose properly presence or absence, and position (three-dimensional position), of the positron-emitting radioisotope distributed in the pair of first sites of interest K1 (breasts) and the second sites of interest K2 (axillary lymph nodes), a grade of malignancy and so on. As a result, the burden of the patient M can also be reduced.

Figure 10:
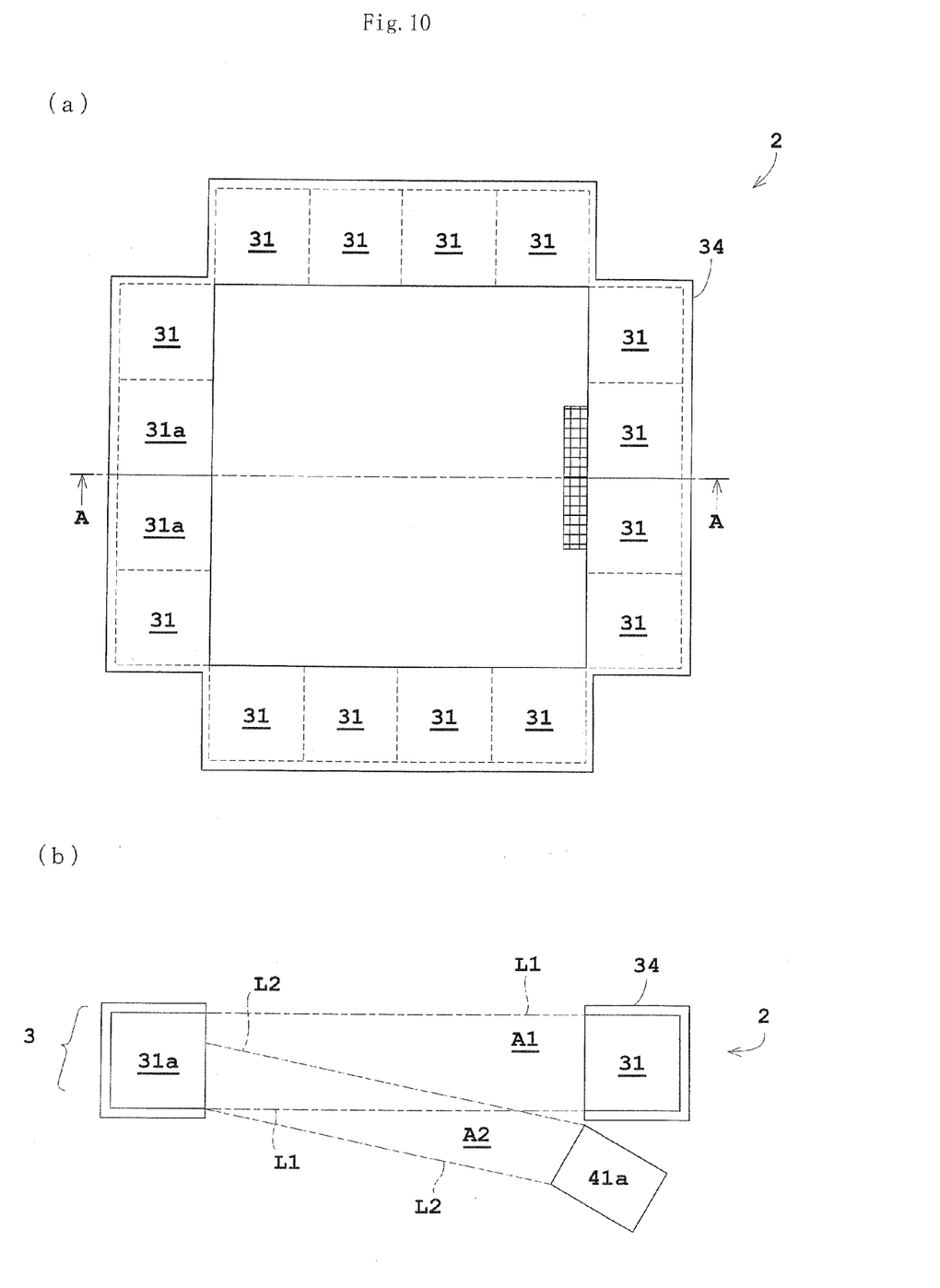

This invention is not limited to the foregoing embodiments, but may be modified as follows:

(1) In Embodiments 1 and 2 described hereinbefore, the first detecting device 1 is ring-shaped, but this is not limitative. Reference is made to FIG. 10. FIG. 10 (a) is a plan view of a first and a second detecting devices according to a modified embodiment. FIG. 10 (b) is a view in vertical section taken on line A-A of FIG. 10 (a). As shown, a first detecting device 2 has gamma-ray detectors 31 arranged along each side of a square, and a housing 34 for accommodating and holding the gamma-ray detectors 31. The range surrounded by the gamma-ray detectors 31 is hollow. Thus, the first detecting device 2, even when changed to what is called the polygonal type, can properly bound peripheries of the first site of interest K1. The polygonal type is not limited to a square, but may be varied to an n-angled figure (n being 3 or larger integer) as appropriate.

Or a modification may be made to have newly a drive mechanism for moving the first detecting device 1 around the first site of interest K1. Where such a drive mechanism is provided, it is not absolutely necessary for the first detecting device 1 to surround the first site of interest K1 in a stationary state. For example, the first detecting device may be constructed to be a set of detecting devices on two, opposite sides of the first site of interest K1, with the drive mechanism moving the set of these detecting devices around the first site of interest K1. Then, the first detecting device can detect gamma rays released from around the first site of interest K1.

(2) Embodiment 2 described hereinbefore includes the detector blocks 41a and 41b arranged at opposite sides of the first detecting device 1, and gamma-ray detectors 31a and 31b of the first detecting device 1, but this is not limitative. Reference is made to FIG. 10 again. As shown, the construction may include a detector block 41a disposed only at one side of the first detecting device 1, and gamma-ray detecting device 31a opposed thereto. In this way, the construction of the second detecting device 3 can be further simplified.

(3) In the first embodiment 1 described hereinbefore, considering the relative positional relationship of the first and second detecting devices 1 and 3, the calculated planar image calculating unit 25 determines a data range corresponding to an area where the first and second imaging areas A1 and A2 overlap in the 3D image, and calculates the calculated planar image from this determined data range. In Embodiment 2 described hereinbefore, the calculated planar image calculating unit 25 calculates the calculated planar image using the entire 3D image, and the correcting unit 27 carries out an alignment of the real planar image and calculated planar image by taking into consideration the relative positional relationship between the first and second detecting devices 1 and 3. In this way, the procedure of the image processor 15 can be selected or varied as appropriate.

(4) In each embodiment described hereinbefore, the first detecting device 1 and combined detecting device 5 are both multilayer rings having the scintillator chips 36 arranged in multiple layers. This is not limitative. A modification may be made to arrange the scintillator chips 36 in one layer. The first image processing unit 21 and image processor 16 serve to produce 3D images. Instead, they may be modified to produce sectional images. The 3D image and sectional image correspond to the RI distribution image in this invention.

(5) In each embodiment described hereinbefore, the gamma detectors 31 are constructed of scintillator 35, light guide 37 and photomultiplier 39. Their construction may be selected or varied as appropriate. For example, the number of arrays and the number of layers of scintillator chips 36 which form the scintillator 35 may be changed as appropriate. The photomultiplier 39 may be changed to a position sensitive PMT (PS-PMT) which can discriminate emission positions. Further, it may be changed to a semiconductor camera with detecting elements formed of cadmium telluride (CdTe) which is a semiconductor, for detecting charges produced by incidence of gamma rays. In this case, the first detecting device 1 and second detecting device 3 may be formed of the same gamma-ray detectors, or may be formed of different gamma-ray detectors.

(6) In each embodiment described hereinbefore, the breasts are regarded as the first site of interest K1 and the axillary lymph nodes as the second site of interest K2. This is not limitative. At least one of the first and second sites of interest K1 and K2 may be replaced with other sites as appropriate. Although the patient M has been the human body, this is not limitative, and can be changed as appropriate to a small animal other than the human body.

INDUSTRIAL UTILITY

As described above, this invention is suitable for diagnosing at the same time two different sites of interest, e.g. the breasts and sentinel lymph nodes thereof.

The invention claimed is:

1. A positron computed tomography (CT) apparatus for detecting gamma rays released from a patient, comprising:
a first detecting device for detecting gamma rays around a first site of interest of the patient;
a second detecting device for detecting gamma rays, which is disposed separately across part of the first site of interest and a second site of interest spaced from an imaging area of the first detecting device;
a first image processing device for producing an Radio Isotope (RI) distribution image from coincidence data obtained from the first detecting device;
a second image processing device for producing a real planar image corresponding to gamma rays released in a predetermined projecting direction, based on coincidence data obtained from the second detecting device;
a calculated planar image calculating device for calculating, based on the RI distribution image produced, a calculated planar image of a time when the imaging area of the first detecting device is projected in the same direction as the projecting direction; and
a correcting device for subtracting the calculated planar image from the real planar image.

2. The positron CT apparatus according to claim 1, wherein the first site of interest is a breast, and the second site of interest is a sentinel lymph node of the breast.

3. The positron CT apparatus according to claim 1, wherein the second detecting device has an imaging area thereof obliquely crossing the imaging area of the first detecting device.

4. The positron CT apparatus according to claim 1, wherein the second detecting device is in an opposed arrangement.

5. The positron CT apparatus according to claim 1, wherein:
the first detecting device acts also as one part of the second detecting device arranged separately; and
the second image processing device produces the real planar image based on coincidence data obtained from the second detecting device and the first detecting device.

6. The positron CT apparatus according to claim 1, wherein the second detecting device is arranged at opposite sides of the first detecting device.

7. The positron CT apparatus according to claim 1, wherein the first detecting device is arranged in a ring form or polygonally.

8. The positron CT apparatus according to claim 1, wherein the RI distribution image is a 3D image.

* * * * *